United States Patent [19]
Asakura et al.

[11] Patent Number: 6,146,860
[45] Date of Patent: Nov. 14, 2000

[54] MANUFACTURE OF L-ASCORBIC ACID AND D-ERYTHORBIC ACID

[75] Inventors: Akira Asakura, Fujisawa; Tatsuo Hoshino, Kamakura; Tatsuya Kiyasu, Fujisawa; Masako Shinjoh, Kamakura, all of Japan

[73] Assignee: Roche Vitamins Inc., Parsippany, N.J.

[21] Appl. No.: 09/484,966

[22] Filed: Jan. 18, 2000

[30] Foreign Application Priority Data

Jan. 18, 1999 [EP] European Pat. Off. .............. 99100785

[51] Int. Cl.$^7$ ............................... C12P 17/04; C12N 9/18
[52] U.S. Cl. .......................... 435/126; 435/137; 435/195; 435/196; 435/197
[58] Field of Search .................................. 435/126, 137, 435/195, 196, 197

[56] References Cited

U.S. PATENT DOCUMENTS

| | | | |
|---|---|---|---|
| 4,259,443 | 3/1981 | Danehy . | |
| 5,817,490 | 10/1998 | Hubbs | 435/137 |
| 5,859,262 | 1/1999 | Meir-Eyal et al. | 435/126 |

FOREIGN PATENT DOCUMENTS

| | | | |
|---|---|---|---|
| 196 04 798 A1 | 8/1997 | Germany . | |
| WO97/43433 | 11/1999 | WIPO . | |

OTHER PUBLICATIONS

Ogawa, et al., "Microbial enzymes: new industrial applications from traditional screening methods," *TIBTECH*, vol. 17, pp. 13–20 (1999).

Kobayashi, et al., "Lactone–ring–cleaving enzyme: Genetic analysis, novel RNA editing, and evolutionary implications," *Proc. Natl. Acad. Sci. USA*, vol. 95, pp. 12787–12792 (2998).

Bublitz, et al., "The role of aldonolactonase in the conversion of L–gulonate to L–ascorbate," *Biochimica et Biophysica*, vol. 47, pp. 288–297 (1961).

Derwent English language abstract of De 196 04 798 A1 (document B2).

Zachariou, et al., "Glucose–Fructose Oxidoreductase, a New Enzyme Isolated from *Zymomonas mobilis* That is Responsible for Sorbitol Production," *Journal of Bacteriology*, 167(3): 863–869 (1986).

Hucho, et al., "Glucono–δ–Lactonase From *Escherichia Coli*," *Biochimica et Biophysica Acta*, 276:176–179 (1982).

Shimizu, et al., "Purification and Characterization of a Novel Lactonohydrolase, Catalyzing the Hydrolysis of Aldonate Lactones and Aromatic Lactones, from *Fusarium oxysporum*," *Eur. J. Biochem.*, 209:383–390 (1992).

Kanagasundaram, et al., "Isolation and Characterization of the gene encoding gluconolactonase from *Zymomonas mobilis*," *Biochimica et Biophysica Acta*, 1171: (1992).

*Primary Examiner*—Herbert J. Lilling
*Attorney, Agent, or Firm*—Mark E. Waddell; Stephen M. Haracz; Bryan Cave LLP

[57] ABSTRACT

A process for producing L-ascorbic acid (vitamin C) from 2-keto-L-gulonic acid or D-erythorbic acid from 2-keto-D-gluconic acid by contacting 2-keto-L-gulonic acid or 2-keto-D-gluconic acid, respectively, in solution with a lactonase, particularly one belonging to the enzyme class EC 3.1.1.x, according to the classification of Enzyme Nomenclature. The solvent for this reaction can be water, an aqueous alcohol, a non-alcoholic organic solvent or a mixture of an aqueous alcohol and a non-alcoholic organic solvent. The contacting is generally performed in a temperature range of 0° C. to 120° C. and a pH range of 1.5 to 12. In each case the starting material can be in the form of the free acid, the sodium salt, or the calcium salt. The so-produced vitamin C has very well known uses, and the alternatively produced D-erythorbic acid is useful as an antioxidant for food additives.

15 Claims, No Drawings

MANUFACTURE OF L-ASCORBIC ACID AND D-ERYTHORBIC ACID

FIELD OF THE INVENTION

The present invention relates to a novel process for producing L-ascorbic acid (vitamin C) or D-erythorbic acid from 2-keto-L-gulonic acid or 2-keto-D-gluconic acid, respectively, using a lactonase.

BACKGROUND OF THE INVENTION

L-ascorbic acid has been produced from 2-keto-L-gulonic acid by the well-known Reichstein method (Helv. Chim. Acta 17, 311–328 (1934)). The method has been used commercially for more than 60 years with many chemical and technical modifications to improve the efficiency of each of the steps to the compounds D-glucose, D-sorbitol, L-sorbose, diacetone-L-sorbose, diacetone-2-keto-L-gulonic acid, 2-keto-L-gulonic acid, and methyl 2-keto-L-gulonate, and L-ascorbic acid. In this process, the conversion of D-sorbitol to L-sorbose is the sole microbial step, the others being chemical steps. The conversion of diacetone-2-keto-L-gulonic acid into L-ascorbic acid is achieved by two different procedures: 1) deprotection to give 2-keto-L-gulonic acid, followed by esterification with methanol and base-catalyzed cyclization; and 2) acid-catalyzed cyclization to L-ascorbic acid directly from the protected or deprotected 2-keto-L-gulonic acid. The starting material for base-catalyzed reactions is methyl 2-keto-L-gulonate, itself prepared by treatment of the acid with acidic methanol. An alternative reaction of the methyl ester with sodium bicarbonate or sodium acetate produces sodium L-ascorbate. Many chemical and technical modifications have improved the efficiency of each step, enabling the multistep synthesis to remain the principally used and economical process.

D-Erythorbic acid has been produced from D-glucose via 2-keto-D-gluconic acid, which itself can be produced by fermentation with a strain belonging to the genus Pseudomonas, and methyl 2-keto-D-gluconate. D-Erythorbic acid is mainly used as an antioxidant for food additives.

Much time and effort has been devoted to finding other methods of synthesizing L-ascorbic acid by microorganisms. Most microbial productions of L-ascorbic acid have been focused on the production of an intermediate of L-ascorbic acid production, 2-keto-L-gulonic acid, from L-sorbose (G. Z. Yin et al., Wei Sheng Wu Hsueh Pao. 20, 246–251 (1980); A. Fujiwara et al., EP 213 591 (Roche); T. Hoshino et al., U.S. Pat. No. 4,960,695 (Roche); and I. H. Nogami et al., EP 221 707), from D-sorbitol (A. Fujiwara et al., EP 213 591 (Roche); T. Hoshino et al., U.S. Pat. No. 5,312,741 (Roche); M. Niwa et al., WO 95/23220; and S. F. Stoddard et al., WO 98/17819), or from D-glucose via 2,5-diketogluconic acid with a single, mixed or recombinant culture (T. Sonoyama et al., Appl. Environ. Microbiol. 43, 1064–1069 (1982); and S. Anderson et al., Science 230, 144–149 (1985)). The 2-keto-L-gulonic acid can then be converted into L-ascorbic acid by chemical means as described above.

The involvement of an enzymatic process for the conversion of the 2-keto-L-gulonic acid ester into L-ascorbic acid has recently been reported (J. C. Hubbs, WO 97/43433 (Eastman Chemical Company)). WO 97/43433 describes a process for allegedly preparing L-ascorbic acid by contacting 2-keto-L-gulonic acid or an ester thereof with a hydrolase enzyme catalyst selected from the group consisting of a protease, an esterase, a lipase and an amidase. Using a hydrolase such as a protease, an esterase, a lipase or an amidase, WO 97/43433 exemplifies the formation of L-ascorbic acid from an ester of 2-keto-L-gulonic acid (butyl 2-keto-L-gulonate), but no apparent formation of L-ascorbic acid from 2-keto-L-gulonic acid itself. WO 97/43433 discloses, for example, that *Candida antartica* B lipase catalyzed the reaction to form 413–530 mg/l of methyl 2-keto-L-gulonate, but no L-ascorbic acid, from 1% 2-keto-L-gulonic acid in the presence of 8.6% methanol at pH 3.1–3.2 at 38° C. Ester synthetic activity of *Candida antartica* B lipase on 2-keto-L-gulonic acid, an α-keto-carboxylic acid, at acidic pH is apparently positive, but intramolecular ester formation by this lipase was negligible. It does not disclose a lactonase as the hydrolase enzyme catalyst for the purpose of producing L-ascorbic acid from 2-keto-L-gulonic acid.

Surprisingly, it has now been found that the conversion of 2-keto-L-gulonic acid to L-ascorbic acid can be performed by a lactonase enzyme. Accordingly, it has been surprising found that the selectivity of lactonase on cyclic esters is favorable for the production of L-ascorbic acid from 2-keto-L-gulonic acid.

Many kinds of lactonases are known, including gluconolactonase (EC 3.1.1.17) of *Escherichia coli* (F. Hucho et al., Biochem. Biophys. Acta 276, 176–179 (1972)) or of *Zymomonas mobilis* (M. Zachariou et al., J. Bacteriol. 167, 863–869 (1986) and V. Kanagasundaram et al., Biochem. Biophys. Acta 1171, 198–200 (1992)), and lactonohydrolase of *Fusarium oxysporum* (S. Shimizu et al., Eur. J. Biochem. 209, 383–390 (1992)). Further reported lactonases include L-arabinonolactonase (EC 3.1.1.15) and D-arabinonolactonase (EC 3.1.1.30) of *Pseudomonas saccharophilia*, L-rhamnono- 1,4-lactonase (EC 3.1.1.65) of *Pullularea pullulans*, xylono-1,4-lactonase (EC 3.1.1.68) of *Pseudomonas fragi* and *Gluconobacter oxydans*, cellobino-lactonase of *Trichoderma reesei* (Chem.-Ztg. 113, 122–124 (1989)), 1,4-lactonase (EC 3.1.1.25), and lactonases with the EC numbers 3.1.1.19, 3.1.1.24, 3.1.1.27, 3.1.1.36, 3.1.1.37, 3.1.1.38, 3.1.1.39, 3.1.1.45, 3.1.1.46, and 3.1.1.57.

Among the lactonases, the lactonohydrolase of *Fusarium oxysporum* has been developed for the industrial asymmetric hydrolysis of D-pantoyl lactone (K. Sakamoto et al., U.S. Pat. No. 5,275,949). The enzyme catalyzes the hydrolysis of a relatively broad range of lactone compounds, including D-pantoyl lactone and several aldonolactones, e.g. D-glucono-δ-lactone and D-galactono-γ-lactone, and the reverse reaction, lactonization.

Nucleotide sequences are available for the genes of some lactonases, i.e., the gluconolactonase gene of *Zymomonas mobilis* (960 bp; 320 amino acid residues; V. Kanagasundaram et al., Biochem. Biophys. Acta 1171, 198–200 (1992)) and the lactonohydrolase gene of *Fusarium oxysporum* (1,140 bp; 380 amino acid residues; K. Sakamoto et al., WO 97/10341).

DETAILED DESCRIPTION OF THE INVENTION

Accordingly, the present invention provides a process for producing L-ascorbic acid from 2-keto-L-gulonic acid, and also a process for producing D-erythorbic acid from 2-keto-D-gluconic acid, in both cases using lactonase enzymes.

More specifically, the present invention is directed to a process for producing L-ascorbic acid from 2-keto-L-gulonic acid or D-erythorbic acid from 2-keto-D-gluconic acid, by contacting 2-keto-L-gulonic acid or 2-keto-D-gluconic acid, respectively, in solution with a lactonase.

The lactonase enzymes used in the process of the present invention may be obtained from any appropriate organisms, including animals, plants, and microorganisms, such as fungi, yeasts and bacteria. Any microorganism may be a functional equivalent, subculture, mutant or variant thereof.

Lactonase (also known as lactonohydrolase) enzymes that are suitable for use in the process of the present invenion are those belonging to the enzyme class EC 3.1.1.x according to the classification of Enzyme Nomenclature (1992, Academic Press). In the designation "EC 3.1.1.x", x signifies any number preceded by "EC 3.1.1." featured by a lactonase, e.g., lactonohydrolase, enzyme belonging to the pertinent class. Examples of such numbers x are featured by the enzyme class designations of the examples of lactonases given above. Lactonase catalyzes reversible reactions, in particular hydrolyzing a lactone, which is a cyclic ester formed from an intramolecular reaction between a carboxyl and a hydroxyl group, and reforming the lactone. A preferred lactonase is a gluconolactonase (EC 3.1.1.17), especially those of *Escherichia coli* and *Zymomonas mobilis*. The lactonohydrolase of *Fusarium oxysporum* is a further preferred lactonase. More specifically preferred lactonases are the gluconolactonase of *Escherichia coli* IFO 14410 or *Zymomonas mobilis* IFO 13756 and the lactonohydrolase of *Fusarium oxysporum* IFO 5942.

The physico-chemical properties of the purified or partially purified gluconolactonases or lactonohydrolase prepared as described in the Examples below are as follows:

1) Enzyme Activity

The lactonases used in the process of the present invention catalyze the lactonization of aldonic acids and are capable of producing aldonolactones without any other co-factors. The enzyme assay for L-ascorbic acid or D-erythorbic acid formation was performed at 50 to 70° C. by measuring the amount of L-ascorbic acid or D-erythorbic acid formed from 2-keto-L-gulonic acid or 2-keto-D-gluconic acid, respectively. For the enzyme purification, the enzyme activity was determined at room temperature (about 20–25° C.) as the lactonase activity on D-galactono-γ-lactone as the substrate to form D-galactonic acid, using p-nitrophenol as a pH indicator. Acidification by the produced D-galactonic acid was detected as a decrease of absorbance of the p-nitrophenol at 405 nm.

2) Optimum pH

The correlation between the reaction rate of lactonase and pH was determined in 0.2 M sodium 2-morpholinoethanesulfonate (Na-MES) buffer (pH 5.5–7.0) or 0.2 M sodium acetate buffer (pH 3.75–5.5) using sodium 2-keto-L-gulonate monohydrate as the substrate at 30, 37, 45, or 55° C. The optimum pHs of *Escherichia coli* gluconolactonase, *Zymomonas mobilis* gluconolactonase and *Fusarium oxysporum* lactonohydrolase were 5.5, 5.5, and 4.5 to 5.0, respectively.

3) Optimum Temperature

The enzyme activities of the lactonases were measured at temperatures from to 30° C. to 70° C. in the reaction mixture with 0.2 M Na-MES buffer (pH 5.5) or 0.2 M sodium acetate buffer (pH 5.0). The optimum temperatures of *Escherichia coli* gluconolactonase, *Zymomonas mobilis* gluconolactonase and *Fusarium oxysporum* lactonohydrolase were 70° C., 50° C., and 55° C., respectively.

4) Molecular Weight

The molecular weights of purified or partially purified lactonases were confirmed on SDS-polyacrylamide gel electrophoresis (SDS-PAGE). Rabbit skeletal muscle phosphorylase B (97,400), bovine serum albumin (66,200), bovine ovalbumin (45,000), bovine carbonic anhydrase (31,000), soybean trypsin inhibitor (21,500) and hen egg white lysozyme (14,400) were used as the molecular weight standards. As a result, the molecular weights of the subunit of *Zymomonas mobilis* gluconolactonase and of *Fusarium oxysporum* lactonohydrolase were confirmed to be about 32 kDa and about 60 kDa, respectively.

The process of the present invention may also be carried out by using a functional derivative of the lactonase. Such functional derivatives differ from the lactonase itself by addition, insertion, deletion and/or substitution of one or more amino acid residues in the normal sequence of the (unmodified) lactonase, whereby such derivatives still have lactonase activity as measured by an assay known in the art or specifically described herein. Such functional derivatives can be made either by chemical peptide synthesis, chemical modification of protein known in the art, or by recombinant means on the basis of the DNA sequences as disclosed herein by methods known in the art and disclosed, for example, by Sambrook et al. (Molecular Cloning, Cold Spring Harbour Laboratory Press, New York, USA, second edition 1989). Amino acid exchanges in proteins and peptides which do not generally alter the activity of such molecules are known in the art and are described, for example, by H. Neurath and R. L. Hill in "The Proteins" (Academic Press, New York, 1979; see especially FIG. 6, page 14). The most commonly occurring exchanges are: Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/Gly, as well as the reverse exchanges.

The lactonase used in the process of the present invention may be obtained by the following methods:

Organisms having a desired lactonase can be obtained from nature, commercially, or from cultures grown in an appropriate medium. The lactonase can be used as a whole organism or in the purified or partially purified enzyme form.

When obtaining the lactonase by culturing the appropriate microorganism in a medium, the microorganism is conveniently cultured in an aqueous medium supplemented with appropriate nutrients under aerobic conditions. The cultivation may be conducted at pHs between about 1.5 and about 12. While the cultivation period varies depending upon the pH, temperature and nutrient medium used, a period of 1 to 10 days will generally bring about favorable results. A preferred temperature range for carrying out the cultivation is about 0° C. to about 120° C.

It is usually required that the culture medium contains such nutrients as assimilable carbon sources, digestible nitrogen sources and inorganic substances, vitamins, trace elements, and other growth promoting factors. As assimilable carbon sources, glycerol, D-glucose, D-mannitol, D-fructose, D-arabitol, L-sorbose, D-sorbitol, and the like can be used.

Various organic or inorganic substances may also be used as nitrogen sources, such as yeast extract, meat extract, peptone, casein, corn steep liquor, urea, amino acids, nitrates, ammonium salts, and the like. As inorganic substances, magnesium sulfate, potassium phosphate, ferrous and ferric chlorides, calcium carbonate, and the like may be used.

Isolation and purification of lactonases from the microorganisms after the cultivation can be performed by the following methods well known in the art:

(1) Cells are harvested from the fermentation broth by centrifugation or filtration.

(2) A crude enzyme solution is prepared from the cells by general cell disruption methods such as sonication, homogenization, French press treatment, and treatment with cell lytic enzyme. Extraction by the osmotic shock method or the self lysis method can be applied for the preparation of a crude enzyme solution.

3) The lactonase is isolated and purified from the crude enzyme solution by usual protein purification methods such as ammonium sulfate precipitation, dialysis, ion exchange chromatography, hydrophobic chromatography, gel filtration chromatography, affinity chromatography, and crystallization.

During the enzyme purification of a lactonase, e.g., gluconolactonase of *Escherichia coli* and *Zymomonas mobilis* and lactonohydrolase of *Fusarium oxysporum*, the enzyme activity can be determined with aldonolactones, such as D-galactono-γ-lactone and D-glucono-δ-lactone, as substrates.

The reaction mixture for carrying out the process of the present invention comprises the substrate, i.e. 2-keto-L-gulonic acid or 2-keto-D-gluconic acid, and the lactonase as the catalyst, wherein the lactonase is in the form of a whole organism, in purified or partially purified form, or in the form of a functional derivative, as mentioned above.

The preferred chemical form of the 2-keto-L-gulonic acid and 2-keto-D-gluconic acid is in each case the free acid, its sodium salt or its calcium salt.

The process of the present invention (the enzyme reaction) is conveniently carried out at temperatures from 0° C. to 120° C., preferably from 20° C. to 100° C., and most preferably from 37° C. to 80° C.

Suitable pHs for effecting the enzyme reaction are from 1.5 to 12, preferably from 1.5 to 8, and most preferably from 2.5 to 7.

The concentration of the substrate 2-keto-L-gulonic acid or 2-keto-D-gluconic acid in the reaction mixture is conveniently from 1 to 300 g/l, preferably from 10 to 200 g/l, and most preferably from 50 to 150 g/l.

The reaction is conveniently carried out in water or an aqueous solvent consisting of water and an alcohol or a mixture of several alcohols, i.e., in an aqueous alcohol. Alternatively, it may be carried out in a non-alcoholic organic solvent or a mixture of an organic solvent with an aforementioned aqueous solvent (aqueous alcohol). The alcohol is preferably a $C_{1-6}$-alkanol, such as methanol, ethanol, n-propanol, isopropanol, n-butanol, isobutanol, or tert.butanol. Organic solvents that are suitable include aliphatic hydrocarbons, e.g., heptane and isooctane, alicyclic hydrocarbons, e.g., cyclohexane, and aromatic hydrocarbons, e.g., benzene and toluene. The preferred solvent is water or an aqueous solvent. From an economical and environmental point of view, as little organic solvent as possible is used in the industrial process.

The reaction mixture may further contain an antioxidant, such as 2-mercaptoethanol, dithiothreitol or cysteine, to prevent the degradation of the produced L-ascorbic acid or D-erythorbic acid.

As an alternative to a lactonase itself, the reaction mixture may comprise an organism having lactonase activity.

For the reaction, any form of the lactonase enzyme can be used, in particular an enzyme solution, the immobilized enzyme, intact cells of the organism having lactonase activity, and immobilized cells having lactonase activity.

L-Ascorbic acid can be produced from L-sorbose or D-sorbitol by combination of the organism having the lactonase activity with an organism having L-sorbose/L-sorbosone dehydrogenase and D-sorbitol dehydrogenase (A. Fujiwara et al., EP 213 591 (Roche); T. Hoshino et al., U.S. Pat. No. 4,960,695 (Roche); T. Hoshino et al., U.S. Pat. No. 5,312,741 (Roche)); ex. *Gluconobacter oxydans* DSM 4025 in one-step conversion with one vessel or two-step conversion with two vessels.

The following examples are provided to further illustrate the process of the present invention. These examples are illustrative only and are not intended to limit the scope of the invention in any way.

EXAMPLES

Example 1

(1) Partial Purification of Gluconolactonase from *Zymomonas mobilis* IFO 13756

*Zymomonas mobilis* IFO 13756 was statically grown in 6 l of a medium consisting of 0.5% yeast extract and 2% glucose (pH 6.9) at 30° C. for 22.5 hours. Cells were collected by centrifugation and washed with 10 mM Tris-HCl buffer (pH 7.5) containing 0.1 M NaCl.

During the enzyme purification, all column chromatography was performed at 4° C. The enzyme activity was determined as the hydrolytic activity of D-galactono-γ-lactone by spectrophotometric assay using p-nitrophenol as a pH indicator. The assay mixture contained 100 mM D-galactono-γ-lactone, 50 μg/ml of p-nitrophenol, 10 mM sodium 2-morpholinoethanesulfonate (Na-MES) buffer (pH 6.4) and enzyme. Acidification by the produced D-galactonic acid was detected as a decrease of absorbance at 405 nm.

The cells (11.7 g wet weight) were suspended in 1,200 ml of 30 mM Tris-HCl buffer (pH 8.0) containing 30% sucrose, and then EDTA (pH 8.0) was added at 1 mM. The suspension was kept at room temperature with stirring for 30 minutes. The cells were collected by centrifugation (8,000× g, for 20 minutes at 4° C.) and resuspended in 12 ml of 30 mM Tris-HCl buffer (pH 8.0) containing 30% sucrose. The suspension was diluted by pouring into 1,800 ml of ice-cold 5 mM $MgSO_4.7H_2O$ and kept on ice with stirring for 30 minutes. The resulting suspension was centrifuged (8,000× g, for 20 minutes at 4° C.) to obtain a supernatant as a periplasmic fraction.

To the periplasmic fraction, Na-MES buffer (pH 6.4) and 2-mercaptoethanol were added at 20 mM and 0.1 mM, respectively, and then $(NH_4)_2SO_4$ was added at 1.25 M. The resulting periplasmic fraction was applied to a Butyl-TOYOPEARL 650 S column (40 ml: internal dimensions (ID) 2.5×8.2 cm, TOSOH Co., Tokyo, Japan) equilibrated with 20 mM Na-MES buffer (pH 6.4) containing 0.1 mM 2-mercaptoethanol and 1.25 M $(NH_4)_2SO_4$. After washing the column with the equilibration buffer, the enzyme was eluted with a linear gradient of $(NH_4)_2SO_4$ (1.25–0 M in 20 mM Na-MES buffer (pH 6.4) containing 0.1 mM 2-mercaptoethanol). The active fractions were collected.

After dialysis against 25 mM Na-MES buffer (pH 5.0) containing 0.1 mM 2-mercaptoethanol, the enzyme fraction was applied to a HITRAP SP column (1 ml, Amersham Pharmacia Biotech AB, Sweden) equilibrated with the same buffer. After washing the column with the same buffer, the enzyme was eluted with a linear gradient of NaCl (0–0.5 M NaCl in the same buffer) and the active fractions were collected. The enzyme solution was dialyzed against 20 mM Na-MES buffer (pH 6.4) and then concentrated with CENTRICON 30 (Amicon Inc., MA, USA). The enzyme solution was stored at −80° C. until used.

Finally, an enzyme solution (0.319 mg of protein) containing gluconolactonase was obtained with a purity of about 30% by 440-fold purification from *Zymomonas mobilis*. The subunit size of the enzyme on SDS-PAGE was approximately 32 kDa and was identical with the reported one of *Zymomonas mobilis* ATCC 29191 (Biochem. Biophys. Acta 1171, 198–200 (1992)).

(2) Conversion of 2-keto-L-gulonic Acid to L-ascorbic Acid by Gluconolactonase of *Zymomonas mobilis* IFO 13756

The partially purified gluconolactonase of *Zymomonas mobilis* was used for the conversion of 2-keto-L-gulonic acid to L-ascorbic acid. The reaction mixture included 8% sodium 2-keto-L-gulonate monohydrate, 1 mM $CaCl_2$ and 320 µg/ml of the partially purified enzyme in 200 mM Na-MES buffer (pH 5.5). The reaction was carried out under anaerobic conditions at 50° C. for 20 hours. L-ascorbic acid was assayed by HPLC on a YMC-Pack Polyamine II column (ID 4.6×150 mm; YMC Co., Japan) at 264 nm with the mobile phase solvent containing 70% (v/v) acetonitrile and 15 mM ammonium dihydrogenphosphate at a flow rate of 1.5 ml/minute. 236.3 mg/l of L-ascorbic acid was produced, as shown in Table 1.

was applied to a HITRAP Q column (1 ml, Amersham Pharmacia Biotech AB, Sweden) equilibrated with the same buffer. After washing the column with the same buffer, the enzyme was eluted with a linear gradient of NaCl (0–0.8 M NaCl in the same buffer) and the active fractions were collected.

The enzyme solution was dialyzed against 25 mM Tris-HCl buffer (pH 7.5) and applied to a RESOURCE Q column (1 ml, Amersham Pharmacia Biotech AB, Sweden) equilibrated with the same buffer. After washing the column with the same buffer, the enzyme was eluted with a linear gradient

TABLE 1

| Enzyme | Origin | Reaction condition | | | | | L-Ascorbic acid (mg/l) |
|---|---|---|---|---|---|---|---|
| | | Enzyme sample (µg/ml) | Na-2KGA.$H_2O$*[3] (%) | pH | Temp. (° C.) | Period (h) | |
| Gluconolactonase*[1] | Zymomonas mobilis | 320 | 8.0 | 5.5 | 50 | 20 | 236.3 |
| no enzyme | | 0 | 8.0 | 5.5 | 50 | 20 | 1.3 |
| Gluconolactonase*[2] | Escherichia coli | 269 | 8.0 | 5.5 | 70 | 20 | 30.5 |
| no enzyme | | 0 | 8.0 | 5.5 | 70 | 20 | 4.0 |
| Lactonohydrolase | Fusarium oxysporum | 400 | 12.0 | 5.0 | 55 | 20 | 714.8 |
| no enzyme | | 0 | 12.0 | 5.0 | 55 | 20 | 7.2 |

*[1]Enzyme purity: about 30%
*[2]Enzyme purity: below 30%
*[3]Na-2KGA.$H_2O$: sodium 2-keto-L-gulonate monohydrate Example 2
(1) Partial Purification of Gluconolactonase from *Escherichia coli* C600 (IFO 14410)

*Escherichia coli* C600 was grown in 6 l of Luria Broth containing 0.2% glucose at 37° C. for 5 hours. Cells were collected by centrifugation and washed with 10 mM Tris-HCl buffer (pH 7.5) containing 0.1 M NaCl.

During the enzyme purification, all column chromatography was performed at 4° C. The enzyme activity was determined spectrophotometrically as described in Example 1. The assay mixture contained 200 mM D-galactono-γ-lactone, 50 µg/ml of p-nitrophenol, 10 mM Na-MES buffer (pH 6.4) and enzyme. Acidification by the produced D-galactonic acid was detected as a decrease of absorbance at 405 nm.

The cells (15.4 g wet weight) were suspended in 1,200 ml of 30 mM Tris-HCl buffer (pH 8.0) containing 30% sucrose, and then EDTA (pH 8.0) was added at 1 mM. The suspension was kept at room temperature with stirring for 30 minutes. The cells were collected by centrifugation (8,000× g, for 20 minutes at 4° C.) and resuspended in 12 ml of 30 mM Tris-HCl buffer (pH 8.0) containing 30% sucrose. The suspension was diluted by pouring into 1,800 ml of ice-cold 5 mM $MgSO_4.7H_2O$ and kept on ice with stirring for 30 minutes. The resulting suspension was centrifuged (8,000× g, for 20 minutes at 4° C.) to obtain a supernatant as a periplasmic fraction.

To the periplasmic fraction, Tris-HCl buffer (pH 7.5) and 2-mercaptoethanol were added at 25 mM and 0.1 mM, respectively, and then $(NH_4)_2SO_4$ was added at 1.5 M. The resulting periplasmic fraction was applied to Butyl-Toyopearl 650 S column (40 ml: ID 2.5×8.2 cm, TOSOH Co. Tokyo, Japan) equilibrated with 25 mM Tris-HCl buffer (pH 7.5) containing 0.1 mM 2-mercaptoethanol and 1.5 M $(NH_4)_2SO_4$. After washing the column with the equilibration buffer, the enzyme was eluted with a linear gradient of $(NH_4)_2SO_4$ (1.5–0 M in 25 mM Tris-HCl buffer (pH 7.5) containing 0.1 mM 2-mercaptoethanol) and the active fractions were collected.

After dialysis against 25 mM Tris-HCl buffer (pH 7.5) containing 0.1 mM 2-mercaptoethanol, the enzyme fraction of NaCl (0–0.6 M NaCl in the same buffer) and the active fractions were collected. The enzyme solution was dialyzed against the same buffer and then concentrated with CENTRICON 30 (Amicon Inc. MA, USA). Finally, an enzyme solution (0.291 mg protein) containing gluconolactonase was obtained by 500-fold purification from *Escherichia coli*. At least five protein bands were observed on SDS-PAGE. The enzyme solution was stored at −80° C. until used.
(2) Conversion of 2-keto-L-gulonic Acid to L-ascorbic Acid by Gluconolactonase of *Escherichia coli* C600 (IFO 14410)

The partially purified gluconolactonase of *Escherichia coli* was used for the conversion activity of 2-keto-L-gulonic acid to L-ascorbic acid. The reaction mixture consisted of 8% sodium 2-keto-L-gulonate monohydrate, 1 mM $CaCl_2$ and 269 µg/ml of the partially purified enzyme in 200 mM Na-MES buffer (pH 5.5). The reaction was carried out under anaerobic conditions at 70° C. for 20 hours, and L-ascorbic acid was assayed by HPLC as described in Example 1. 30.5 mg/l of L-ascorbic acid were produced, as shown in Table 1.

Example 3
(1) Purification of Lactonohydrolase from *Fusarium oxysporum* IFO 5942

*Fusarium oxysporum* lactonohydrolase was purified from IFO 5942 strain according to the methods described in the literature (S. Shimizu et al., Eur. J. Biochem. 209, 383–390 (1992)). The enzyme was purified by monitoring of gluconolactonase activity. The activity was determined by the method described in Example 1. The assay mixture contained 25 mM D-galactono-γ-lactone, 0.25 mM p-nitrophenol, 20 mM sodium 3-morpholino-1-propanesulfonate buffer (pH 7.2) and 1 mM $CaCl_2$. Acidification by the produced D-galactonic acid was detected as a decrease of absorbance at 405 nm.

*Fusarium oxysporum* IFO 5942 was grown in 7.5 l of modified Czapek medium containing 3% sucrose, 0.4% $NaNO_3$, 0.2% $K_2HPO_4$, 0.1% $MgSO_4.7H_2O$, 0.05% KCl, 0.001% $FeSO_4.7H_2O$, 0.002% $ZnSO_4.7H_2O$ (pH 6.0) at 28° C. for 48 hours. The cells were collected by filtration with WHATMAN 1SP filter (Whatman NJ, UK) and washed with "TB buffer", consisting of 20 mM Tris-HCl (pH 7.4) containing 0.1 mM dithiothreitol, to obtain 365 g of wet cells. The cells were suspended in 1 l of TB buffer and incubated at 10–15° C. for 7 days under the pH maintained at 6.0 to 6.2 by adding 2 M $Na_2CO_3$. The resulting cell suspension was filtrated with WHATMAN 1SP filter and the resulting filtered solution was centrifuged to remove cell debris; about 1 l of supernatant was separated from the cells. The supernatant was dialyzed against 5 l of TB buffer to obtain 1200 ml of the cell extract containing 408 mg of total proteins. The cell extract was first applied to DEAE-TOYOPEARL 650M (TOSOH Co., Tokyo, Japan, ID 4.4×4 cm, 60 ml, equilibrated with TB buffer). After washing with 1 l of TB buffer, proteins were eluted by a 540 ml of 0–0.3 M NaCl linear gradient in TB buffer. The active fractions were collected, dialyzed against 2 l of TB buffer and applied to SUPERQ-TOYOPEARL 650M (TOSOH Co., Japan, ID 1.5×8 cm, 14 ml, equilibrated with TB buffer). After washing with 20 ml of TB buffer, the proteins were eluted by a 240 ml of 0–0.15 M NaCl linear gradient in TB buffer. The active fractions (30 ml) were collected and diluted with 20 ml of TB buffer (final protein concentration of about 1 mg/ml). To the 50 ml of resulting enzyme solution, 0.5 ml of 2 M Tris-HCl (pH 8.25) and 30 g of solid ammonium sulfate were added (approx. 85% saturation of ammonium sulfate) and incubated at 4° C. for 10 minutes. Precipitated proteins were removed by centrifugation at 15,000 rpm for 30 minutes. For removal of ammonium sulfate, the supernatant with the enzyme activity was extensively dialyzed against TB buffer by repeated concentration and dilution in a concentrator with YM-30 filter (Amicon Inc., MA, USA). After dialysis and concentration (to less than 10 ml), the enzyme started to precipitate as crystals (microneedles). The crystallized enzyme was collected by centrifugation, washed twice with TB buffer and dissolved in TB buffer containing 0.1 M KCl at a concentration of 2.0 mg/ml protein as the purified enzyme. Finally, 2 mg of the purified enzyme showing a single 60 kDa band on SDS-PAGE were obtained from the cell extract with about 56-fold purification factor and 27% recovery yield. The purified enzyme was stored at −80° C. until used.

(2) Conversion of 2-keto-L-gulonic Acid to L-ascorbic Acid by Lactonohydrolase of *Fusarium oxysporum* IFO 5942

The purified lactonohydrolase of *Fusarium oxysporum* was used for the conversion of 2-keto-L-gulonic acid to L-ascorbic acid. The reaction mixture consisted of 12% sodium 2-keto-L-gulonate monohydrate, 0.2 M sodium acetate buffer (pH 5.0) and 1 mM $CaCl_2$. The reaction was carried out at 55° C. for 20 hours under anaerobic conditions, and the produced L-ascorbic acid was assayed by HPLC as described in Example 1. The reaction mixtures containing 400 µg/ml of the purified enzyme produced 714.8 mg/l of L-ascorbic acid. The same reaction condition without the purified enzyme showed 7.2 mg/l of L-ascorbic acid accumulation as background, as shown in Table 1.

(3) Ester Selectivity of Lactonohydrolase of *Fusarium oxysporum* IFO 5942

Methyl 2-keto-L-gulonate (12% w/v), lactonohydrolase of *Fusarium oxysporum* IFO 5942 (100 µg/ml) and 0.2 M Na-MES buffer (pH 7.0) were incubated at 50° C. for 2 hours under argon gas. The lactonohydrolase addition had no effect on methyl 2-keto-L-gulonate consumption.

Linear ester synthetic activity on 2-keto-L-gulonic acid (12%) with methanol (10%) was examined under the following conditions: sodium 2-keto-L-gulonate monohydrate (12% w/v), methanol (10% v/v), lactonohydrolase of *Fusarium oxysporum* IFO 5942 (200 µg/ml), and 0.2 M sodium acetate buffer (pH 5.0) were incubated at 50° C. for 20 hours under argon gas. No methyl 2-keto-L-gulonate was detected, while 219 mg/l of L-ascorbic acid was detected.

Example 4
Conversion Activity of Lipase from 2-keto-L-gulonic Acid to L-ascorbic Acid No activity from 2-keto-L-gulonic acid to L-ascorbic acid was detected in lipase of *Rhizopus delemar*. The reaction mixture consisted of lipase of *Rhizopus delemar* (Lipase RD) purchased from SEIKAGAKU Co. (Code No. 100890, Tokyo, Japan), 6% sodium 2-keto-L-gulonate monohydrate, 0.2 M sodium acetate buffer (pH 5.0), and 1 mM $CaCl_2$. The reaction was carried out at 37° C. for 20 hours under anaerobic conditions, and the produced L-ascorbic acid was assayed by HPLC as described in Example 1. The reaction mixture containing 500 µg/ml Lipase RD produced no detectable amount of L-ascorbic acid (Table 2). Similar reaction conditions with 100 µg/ml of lactonohydrolase of *Fusarium oxysporum* produced 48.3 mg/l of L-ascorbic acid from 3.2% sodium 2-keto-L-gulonate monohydrate, as shown in Table 2.

TABLE 2

| | | Reaction condition | | | | | L-Ascorbic acid (mg/l) |
|---|---|---|---|---|---|---|---|
| Enzyme | Origin | Enzyme sample | Na-2KGA.$H_2O$*[3] | pH | Temp. (° C.) | Period (h) | |
| Lipase | *Rhizopus delemar* | 500 | 6.0 | 5.0 | 37 | 20 | 0 |
| Lactonohydrolase | *Fusarium oxysporum* | 100 | 3.2 | 5.0 | 37 | 20 | 48.3 |
| no enzyme | | 0 | 3.2 | 5.0 | 37 | 20 | 0.5 |

*[1]Na-2KGA.$H_2O$: sodium 2-keto-L-gulonate monohydrate

Example 5
Conversion of 2-keto-D-gluconic Acid to D-erythorbic Acid by Gluconolactonases of *Zymomonas mobilis* IFO 13756 and *Escherichia coli* C600

The partially purified gluconolactonases of *Zymomonas mobilis* and *Escherichia coli* were used for the conversion of 2-keto-D-gluconic acid to D-erythorbic acid. The reaction mixture consisted of 4.7% 2-keto-D-gluconic acid hemicalcium salt (Sigma Chemical Co., St. Louis, Mo., USA) and the gluconolactonase of *Zymomonas mobilis* or *Escherichia coli* in 167 mM Na-MES buffer (pH 5.5). The gluconolactonase of *Zymomonas mobilis* was added at a concentration of 213 µg/ml, and the reaction was carried out under anaerobic conditions at 50° C. for 20 hours. The gluconolactonase of *Escherichia coli* was added at a concentration of 180 µg/ml, and the reaction was carried out under anaerobic conditions at 70° C. for 20 hours. D-Erythorbic acid was assayed by HPLC on YMC-PACK Polyamine II column (ID 4.6×150 mm; YMC Co. Japan) at 264 nm with the mobile phase solvent containing 70% (v/v) acetonitrile and 15 mM ammonium dihydrogenphosphate at a flow rate of 1.5 ml/minute. 35.8 mg/l or 39.6 mg/l of D-erythorbic acid was produced by the gluconolactonase of *Zymomonas mobilis* or *Escherichia coli*, respectively, as shown in Table 3.

TABLE 3

| | | Reaction condition | | | | | D-Erythorbic acid (mg/l) |
|---|---|---|---|---|---|---|---|
| Enzyme | Origin | Enzyme sample (μg/ml) | 2-Keto-D-gluconic acid*[3] (%) | pH | Temp. (° C.) | Period (h) | |
| Gluconolactonase*[1] | *Zymomonas mobilis* | 213 | 4.7 | 5.5 | 50 | 20 | 35.8 |
| no enzyme | | 0 | 4.7 | 5.5 | 50 | 20 | 0.47 |
| Gluconolactonase*[2] | *Escherichia coli* | 180 | 4.7 | 5.5 | 70 | 20 | 39.6 |
| no enzyme | | 0 | 4.7 | 5.5 | 70 | 20 | 2.34 |

*[1]Enzyme purity: about 30%
*[2]Enzyme purity: below 30%
*[3]2-Keto-D-gluconic acid hemi-calcium salt

What is claimed is:

1. A process for preparing L-ascorbic acid from 2-keto-L-gulonic acid or preparing D-erythorbic acid from 2-keto-D-gluconic acid, the process comprising contacting a solution containing 2-keto-L-gulonic acid or 2-keto-D-gluconic acid with a lactonase.

2. A process according to claim 1 wherein the lactonase belongs to the enzyme class EC 3.1.1.x, according to the classification of Enzyme Nomenclature.

3. A process according to claim 2 wherein the lactonase belongs to the enzyme class EC 3.1.1.17.

4. A process according to claim 3 wherein the lactonase is a gluconolactonase obtained from *Escherichia coli* or *Zymomonas mobilis*.

5. A process according to claim 2 wherein the lactonase is a lactonohydrolase obtained from *Fusarium oxysporum*.

6. A process according to claim 1 wherein the lactonase is a lactonase or an organism having lactonase activity.

7. A process according to claim 1 wherein the solvent is water.

8. A process according to claim 1 wherein the solvent is an aqueous solvent selected from the group consisting of water and an alcohol, and water and a mixture of alcohols.

9. A process according to claim 1 wherein 2-keto-L-gulonic acid or 2-keto-D-gluconic acid is contacted with the lactonase at a temperature from 0° C. to 120° C.

10. A process of claim 9 wherein the temperature is from about 20° C. to about 100° C.

11. A process of claim 10 wherein the temperature is from about 37° C. to about 80° C.

12. A process according to claim 1 wherein 2-keto-L-gulonic acid or 2-keto-D-gluconic acid is contacted with the lactonase at a pH from 1.5 to 12.

13. A process according to claim 12 wherein the pH is from about 1.5 to about 8.

14. A process according to claim 13 wherein the pH is from about 2.5 to about 7.

15. A process according to claim 1 wherein the 2-keto-L-gulonic acid or 2-keto-D-gluconic acid is selected from the group consisting of the free acid, the sodium salt, or the calcium salt.

* * * * *

UNITED STATES PATENT AND TRADEMARK OFFICE
CERTIFICATE OF CORRECTION

PATENT NO : 6,146,860
DATED : November 14, 2000
INVENTOR(S) : Akira ASAKURA, et al.

It is certified that error appears in the above-identified patent and that said Letters Patent are hereby corrected as shown below:

On the title page, under [75] Inventors, in each of the cities of residence of the inventors, please change "Fujisawa" to --Fujisawa-shi--, and "Kamakura" to --Kamakura-shi--;

On the title page, under OTHER PUBLICATIONS, in the last listed reference (Kanagasundaram, et al.), please insert --198-200-- after "1171:".

Signed and Sealed this

Fifteenth Day of May, 2001

*Attest:*

NICHOLAS P. GODICI

*Attesting Officer*  *Acting Director of the United States Patent and Trademark Office*